United States Patent [19]
Doth et al.

[11] Patent Number: 6,114,180
[45] Date of Patent: *Sep. 5, 2000

[54] SYNTHETIC CALIBRATORS FOR USE IN IMMUNOASSAYS, COMPRISING THE ANALYTES OR PARTIAL SEQUENCES THEREOF WHICH ARE CONJUGATED TO INERT CARRIER MOLECULES

[75] Inventors: Margit Doth; Christoph Petry, both of Krefeld, Germany

[73] Assignee: Bayer Aktiengesellschaft, Leverkusen, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/671,478

[22] Filed: Jun. 27, 1996

[30] Foreign Application Priority Data

Jul. 6, 1995 [DE] Germany .............. 195 24 572

[51] Int. Cl.[7] ............ A61K 35/34; G01N 33/545; A01N 37/18; C07K 1/00
[52] U.S. Cl. .............. 436/531; 424/569; 514/2; 514/21; 530/350; 530/414; 530/417; 530/814; 530/841; 436/518
[58] Field of Search ............... 424/569; 514/2, 514/21; 530/350, 414, 417, 814, 841; 436/518, 531

[56] References Cited

U.S. PATENT DOCUMENTS

| 5,543,332 | 8/1996 | Lihme et al. | 436/528 |
| 5,560,937 | 10/1996 | Lee et al. | 424/569 |
| 5,583,200 | 12/1996 | Larue et al. | 530/350 |

FOREIGN PATENT DOCUMENTS

0 650 053 A1  5/1995  European Pat. Off. .

OTHER PUBLICATIONS

Pearlstone et al. Can. J. Biochem 63:212–218, 1984.
Chong et al. J. of Bio. Chem 256(10): 5071–5076, 1981.
Leszyk et al. Biochemistry 27:6983–6987, 1988.
S.S. Wong, Chemistry of Protein Conjugation and Cross–Linking, 1991, CRC Press.
S. Yoshitake et al, Conjugation of Glucose Oxidase from Aspergillus . . . , Eur.J.Biochem, 101, 395–399 (1979).
W.J. Vallins et al,Molecular cloning of human cardiac troponin . . . , FEBS 08842, vol. 270, No. 1,2,57–61 (1990).

*Primary Examiner*—James C. Housel
*Assistant Examiner*—V. Ryan
*Attorney, Agent, or Firm*—Norris, McLaughlin & Marcus, P.A.

[57] ABSTRACT

The invention relates to synthetic calibrators for immunological tests, analyte-specific epitopes being coupled to other proteins or to synthetic carriers.

6 Claims, No Drawings

SYNTHETIC CALIBRATORS FOR USE IN IMMUNOASSAYS, COMPRISING THE ANALYTES OR PARTIAL SEQUENCES THEREOF WHICH ARE CONJUGATED TO INERT CARRIER MOLECULES

To detect proteins in serum or urine samples for medical diagnosis purposes, immunoassays are frequently used because of particularly good specificity and sensitivity. For this, in addition to one or two specific antibodies, a calibrator is needed which is used as a comparative standard for the quantification of the patient samples and as a positive control. Particularly for automated assays in large analytical laboratories, storage of the calibrators at 4° C. for several weeks to months is desirable. These demands on the stability of the calibrator formulation can cause difficulties, depending on the analyte, if, for example, solubility under physiological salt and pH conditions is not guaranteed. Examples which may be mentioned here are troponin I and troponin T, which are only adequately stable and soluble in denaturing solutions (6 M urea, 0.01 M dithiothreitol). Using this denaturing formulation, however, an immunoassay cannot be established, as the antibodies are damaged by this treatment.

It is known that proteins have limited stability in solution and that reagents comprising them are frequently marketed in freeze-dried form and have to be dissolved using a solvent of suitable composition before use. If the solutions obtained in this way are stored at 4° C., they can be used for several days even if the daily determination shows a certain change in the concentration of the reagent. Thus in general—and also in the case of troponin I and troponin T—it is recommended to freeze the comparison solutions obtained starting from the freeze-dried material in unit dose form for relatively long storage.

One possibility for the development of a stable calibrator consists in conjugating the entire protein or partial sequences to a carrier molecule and thus increasing the solubility and/or stability. The carrier molecule should in this case be immunologically unreactive, but capable of chemical conjugation.

The present invention relates to a synthetic calibrator having very good stability for use in immunoassays for the determination of medically relevant analytes in blood, plasma, serum or urine samples. The preparation comprises the chemical coupling of the analyte or its partial sequences to immunologically inert conjugable carrier molecules. The synthetic calibrator substance is present in physiological buffers having salt concentrations of 0.01–5 M in particular 0.05–0.5 M and pH conditions between pH 2 and 12, in particular pH 6–8. The buffers can contain preservatives such as sodium azide, Proclin 150, stabilizers such as bovine serum albumin (BSA), human or mouse serum, mouse immuloglobulins, other additives such as β-mercaptoethanol, EDTA, or detergents such as Tween 20, sodium dodecylsulphate (SDS) or Triton X 100.

The chemical conjugation proceeds according to known methods, which are described in the literatre (S. S. Wong, Chemistry of protein conjugation and cross-linking, 1991 CRC Press Inc.).

Cross-linking reagents can be homobifunctional or heterobifunctional. The first react with amino groups, for example glutaraldehyde with the ε-amino group of the lysine, with sulphhydryl groups, for example bismaleimides or alkylating agents, with carboxyl groups, for example carbodiimides in combination with diamines or with phenolates and imidazolyl groups, for example diazonium salts which react with aromatic amino acids such as tyrosine or histidine. Heterobifunctional cross-linkers are furthermore suitable for coupling peptides to carrier molecules. N-Succinmidyl4-(N-maleimidomethyl)cyclohexane-1-carboxylate (SMCC), for example, reacts with amino groups on the one hand and sulphhydryl groups on the other hand. Pyridyl-2,2'-dithiobenzyl diazoacetate (PDD) or p-nitrophenyl diazoacetate, for example, reacts with carboxyl and sulphhydryl or amino groups. 1-Aminooxy4-{(3-nitro-2-pyridyl)dithio}butane, for example, is a reagent which binds carbonyl and sulphhydryl groups. If no sulphhydryl groups are present in the proteins or peptides in question or in the carrier molecule, these can be attached to amino groups, for example of the lysine, by means of 2-iminothiolane hydrochloride (2-IT) or similar reagents.

The carrier molecule can consist of proteins or polymers which contain conjugable groups. Suitable carrier molecules are preferably large proteins (MW>100 kD), such as ferritin, $\alpha_1$-macroglobulin or thyroglobulin, in which, in the case of a sandwich assay, no steric hindrance of the two antibodies is to be expected. However, smaller proteins such as BSA can also be used as a carrier material. Reactive groups in proteins suitable for coupling are, for example, amino groups of the side chains, for example, in lysine or the sulphhydryl group of cysteine.

Suitable synthetic carrier materials are polymers such as polyvinyl alcohols, polyacrylates or polysulphonates, but also polyamides, polyesters and polyethers. The coupling of peptides to these compounds is carried out by means of the corresponding functional groups (hydroxyl, carboxyl or amino groups).

Furthermore, in addition to proteins, natural substances such as chitin and also chitosan or gelatin can be used as carrier materials.

The substance to be conjugated includes proteins relevant to medical diagnosis, which are either bound to the support as the whole or as partial sequences. Suitable partial sequences are fragments formed by protease cleavage or synthetic peptides of the original molecule which are produced with the aid of commercially available synthesizers. In this case, the number of different sequences can be between 1 and 20. For a sandwich assay, i.e. using two antibodies specific for the analyte, a sufficiently long or, better, two different peptides must be bound to the support.

Easier coupling can be possible when the synthetic peptides to be conjugated have a modified (analyte) sequence, e.g. C-terminal attachment of a cysteine or lysine. The peptides should include epitopes for the analyte-specific antibodies; as a rule, these are protein sequences from the surface of the molecule.

The invention relates in particular to a synthetic calibrator material for cardiac troponin I, a cardiospecific protein which plays a part in the diagnosis of acute myocardial infarcts. The calibrator consists of two synthetic peptides of this analyte which have been conjugated to BSA as carrier.

PREPARATION OF A CALIBRATOR ACCORDING TO THE INVENTION

Bovine serum albumin was selected as carrier molecule and the peptides of human cardiac TnI had the following sequences:

Peptide 1: Amino acids 27–40 of the TnI sequence and
Peptide 2: Amino acids 69–85 of the TnI sequence A cysteine was attached at the C-terminus on peptide 1 and alanine and lysine were attached to peptide 2 to facilitate the conjugation. For coupling, a method known for protein conjugation was selected (S. Yoshitake et al., Eur. J.

Biochem., 101, 395, 1979). The carrier protein BSA was activated with SMCC by dissolving 20 mM SMCC in DMF and was added as a 25-fold excess to the BSA. The mixture incubated at 25° C. for 25 min. The reaction was ended by addition of 1 µM of glycine solution (10 min, 25° C.). The peptides were bound to the activated BSA either via the sulphhydryl group in their sequence or by inserting one using 2-IT.

To purify the calibrator substance, i.e. remove the low molecular weight activation substances, gel chromatography (Superdex 200) was carried out. UV spectrometric concentration determination and stabilization by means of 0.5% BSA/0.1% sodium azide were then carried out. Affinity chromatographic purification by means of the sequence-specific antibodies which are also employed in the immunoassay is furthermore possible, or any other common method for protein purification.

Carrying out the Immunoassays

1. ELISA

Using the above mentioned calibrator according to the invention, a sandwich ELISA which shows that the calibrator substance can be used as a replacement for the natural analyte was carried out according to common methods.

An antibody against Sequence 1 of TnI, which was conjugated to the synthetic calibrator, was applied to microtitre plates (Greiner). Incubation with the calibrator was then carried out. The detection antibody used was an antibody produced in goats against the 2nd peptide of TnI, which was coupled to the synthetic calibrator. The binding of this antibody to the synthetic calibrator was detected by means of an antigoat IgG antibody which was conjugated with alkaline phosphatase. This enzyme catalyses colour reactions whose intensity is proportional to the amount of analyte bound in the sandwich. Using this ELISA, it was possible to show that the conjugate is stable for at least 24 h at 37° C.

2. Automated Sandwich Assay

The synthetic calibrator was employed on the automated Immuno 1 analyser (Miles Diagnostics). The assay format was likewise a sandwich using the same antibodies as in the ELISA described under 1. The first antibody of the sandwich binds Sequence 1 on the synthetic calibrator. The antibody is labelled with FITC and is immobilized on magnetic particles by means of anti-FITC. The 2nd antibody of the sandwich carries alkaline phosphatase and catalyses the colour reaction. The antibody incubation was carried out sequentially. It was also possible in this test process to show an increase in the colour intensity which was proportional to the concentration of the calibrator substance.

We claim:

1. A calibrator compound comprising first and second peptides separately coupled to an inert carrier molecule, wherein said first peptide consists of amino acid sequence 27–40 of human cardiac troponin I and said second peptide consists of amino acid sequence 69–85 of human cardiac troponin I.

2. A calibrator according to claim 1, consisting of first and second peptides coupled to an inert carrier molecule, wherein said first peptide consists of the amino acid sequence 27–40 of human cardiac troponin I, said second peptide consists of the amino acid sequence 69–85 of human cardiac troponin I, and said inert carrier molecule is bovine serum albumin.

3. An immunoassay calibration method comprising:

a) incubating an antibody specific for one of said first and second peptides of the calibrator compound of claim 1 and b) determining any binding of said antibody to said calibrator.

4. An immunoassay calibration according to claim 3, in which the carrier molecule is a protein or a polymer.

5. An immunoassay calibration method according to claim 4, wherein the carrier molecule is selected from the group consisting of bovine serum albumin, ferritin, $\alpha_1$-macroglobuin, thyroglobulin, polyvinyl alcohols, polyacrylates, polysulphonates, polyamides, polyesters and polyethers.

6. An immunoassay calibration method according to claim 3, wherein said calibrator compound consists of first and second peptides coupled to an inert carrier molecule, wherein said first peptide consists of the amino acid sequence 27–40 of human cardiac troponin I, said second peptide consists of the amino acid sequence 69–85 of human cardiac troponin I, and said inert carrier molecule is bovine serum albumin.

* * * * *